United States Patent [19]
Hill et al.

[11] Patent Number: 5,857,155
[45] Date of Patent: Jan. 5, 1999

[54] METHOD AND APPARATUS FOR GEOGRAPHIC BASED CONTROL IN A COMMUNICATION SYSTEM

[75] Inventors: Thomas Casey Hill, Trophy Club, Tex.; Bernard Carl Olson, San Carlos, Calif.; George Brooke Neville, Dacula, Ga.; Mark Jordan Appel, Forth worth; Gregory Lewis Cannon, Keller, both of Tex.

[73] Assignee: Motorola, Inc., Schaumburg, Ill.

[21] Appl. No.: 675,318

[22] Filed: Jul. 10, 1996

[51] Int. Cl.⁶ .................................................. H04Q 7/20

[52] U.S. Cl. ........................... 455/456; 455/69; 455/440; 455/522; 342/357; 342/457

[58] Field of Search ..................................... 455/456, 427, 455/430, 502, 517, 522, 440, 441, 63, 69, 38.3, 250.1, 254; 342/357, 457, 418

[56] References Cited

U.S. PATENT DOCUMENTS

| | | | |
|---|---|---|---|
| 5,184,347 | 2/1993 | Farwell et al. | 370/94.1 |
| 5,225,843 | 7/1993 | Thompson | 342/367 |
| 5,235,633 | 8/1993 | Dennison et al. | 455/456 |
| 5,257,408 | 10/1993 | Olson et al. | 455/67 |
| 5,396,647 | 3/1995 | Thompson et al. | 455/440 |
| 5,442,805 | 8/1995 | Sagers et al. | 455/456 |
| 5,469,471 | 11/1995 | Wheatley | 875/205 |
| 5,507,023 | 4/1996 | Suganuma et al. | 455/234.1 |
| 5,548,296 | 8/1996 | Matsuno | 342/457 |

*Primary Examiner*—Wellington Chin
*Assistant Examiner*—Lee Nguyen
*Attorney, Agent, or Firm*—Charles W. Bethards; Pablo Meles

[57] ABSTRACT

A selective call transceiver (20) in a messaging system (100) having a plurality of transmitters (90, 94, 99), comprises a receiver module (26), a transmitter module (22) coupled to the receiver module and a controller (28) coupled to the receiver module and the transmitter module for controlling the operation of the selective call transceiver. Additionally the selective call transceiver comprises a GPS receiver (24) for receiving GPS information and coupled to the controller, wherein the controller uses the GPS information to assist in the control of functions selected from the group consisting of transmitter power control, site selection switching, subzone selection switching, forward error correction, retry transmission decisions, Doppler frequency shifting, synchronization, and frequency scanning and selection.

21 Claims, 4 Drawing Sheets

10
(PRIOR ART)

METHOD AND APPARATUS FOR GEOGRAPHIC BASED CONTROL IN A COMMUNICATION SYSTEM

FIELD OF THE INVENTION

This invention relates in general to use of a global positioning satellite system (GPS) information in a two-way communication system and more specifically to use of GPS receivers to control power and other parameters in a two-way communication system.

BACKGROUND OF THE INVENTION

The advent of two-way paging raises many system issues as well as issues that would require greater efficiency at a portable subscriber unit. With the addition of a transmitter to a traditional one-way paging subscriber unit, battery life becomes more significant than usual. On a system level, a transmitter at the portable subscriber unit provides many benefits that can still use further refinements. For example, a system that does not adjust their transmission power, either from an outbound paging transmitter to a portable subscriber unit or from the portable subscriber unit inbound to the system reduces the overall system efficiency as well as battery life at the subscriber unit. When transmitters needlessly transmit at full power, system capacity is jeopardize and the risk of on-channel intermodulation is increased. There are existing methods that use Received Signal Strength Indicator (RSSI) measurements, Signal Quality Evaluation (SQE) measurements, and/or color codes to adjust transmission power or to make transmission site selection decisions. These methods are adequate in many instances, but they are not accurate. For instance, these methods do not account for the terrain nor do they allow for automatic "boundary" site switching. Geographic information at a portable subscriber unit would thus be helpful in controlling many operations. Thus, a need exists incorporating geographic information for optimizing power transmission levels from either a portable subscriber unit's transmitter or an outbound transmitter. Additionally, geographic information would provide other benefits that would improve site selection decisions, battery life and synchronization among other benefits.

SUMMARY OF THE INVENTION

A transceiver in a communication system having a plurality of transmitters, comprises a receiver module, a transmitter module coupled to the receiver module and a controller coupled to the receiver module and the transmitter module for controlling the operation of the transceiver. Additionally the transceiver comprises a GPS receiver for receiving GPS information and coupled to the controller, wherein the controller uses the GPS information to assist in the control of functions selected from the group consisting of transmitter power control, site selection switching, sub-zone selection switching, forward error correction, retry transmission decisions, Doppler frequency shifting, synchronization, or frequency scanning & selection.

In another aspect of the present invention, a method of controlling the operation of a subscriber device having a GPS receiver within a messaging system having a plurality of transmitters having known coordinates comprises the steps of acquiring GPS information from the GPS receiver and accessing a memory location having known transmitter coordinates and comparing the known transmitter coordinates with the GPS information. Then, the method controls the operation of the messaging system based on the GPS information and the known transmitter coordinates.

DESCRIPTION OF THE PREFERRED EMBODIMENT

Figure 1:
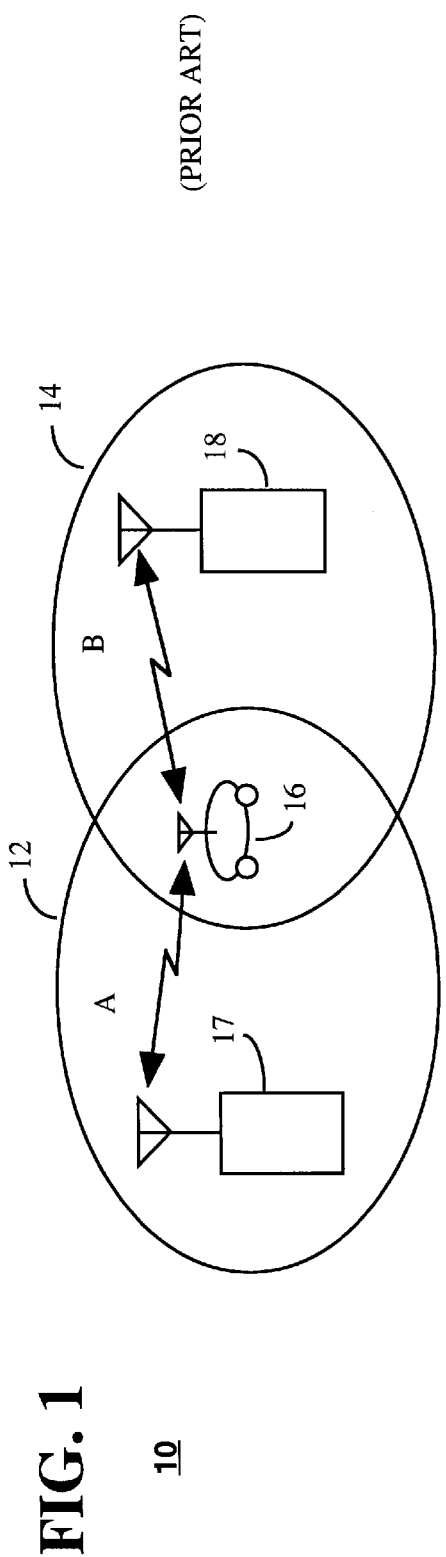
FIG. 1 is a system block diagram of a known two-way messaging system.

Referring to FIG. 1, an existing scenario is shown where a mobile subscriber unit 16 is traveling from Zone A (12) to Zone B (14) within the communication system 10 where the subscriber unit performs a handover from a first base site 17 to second base site 18 and adjusts its transmit power based on RSSI (or SQE) measurements from the second base site 18. However, this information requires over-the-air protocol overhead which could be used for other requirements. Also, a problem exists where handover for a multi-site network may be more advantageous based on geographical boundaries rather than on signal strength. The selection of the best site based on RSSI or SQE, inbound or outbound or both, may not always be the best choice for handover or a targeted message delivery. The use of geographic information (as well as timing information in the case of synchronization) would thus greatly enhance the efficiency and accuracy of such decisions as handover, targeted message delivery and power adjustments. The present invention thus utilizes geographic information (and timing information in the case of synchronization) from a GPS satellite receiver to provide a more robust two-way communication system.

Figure 2:
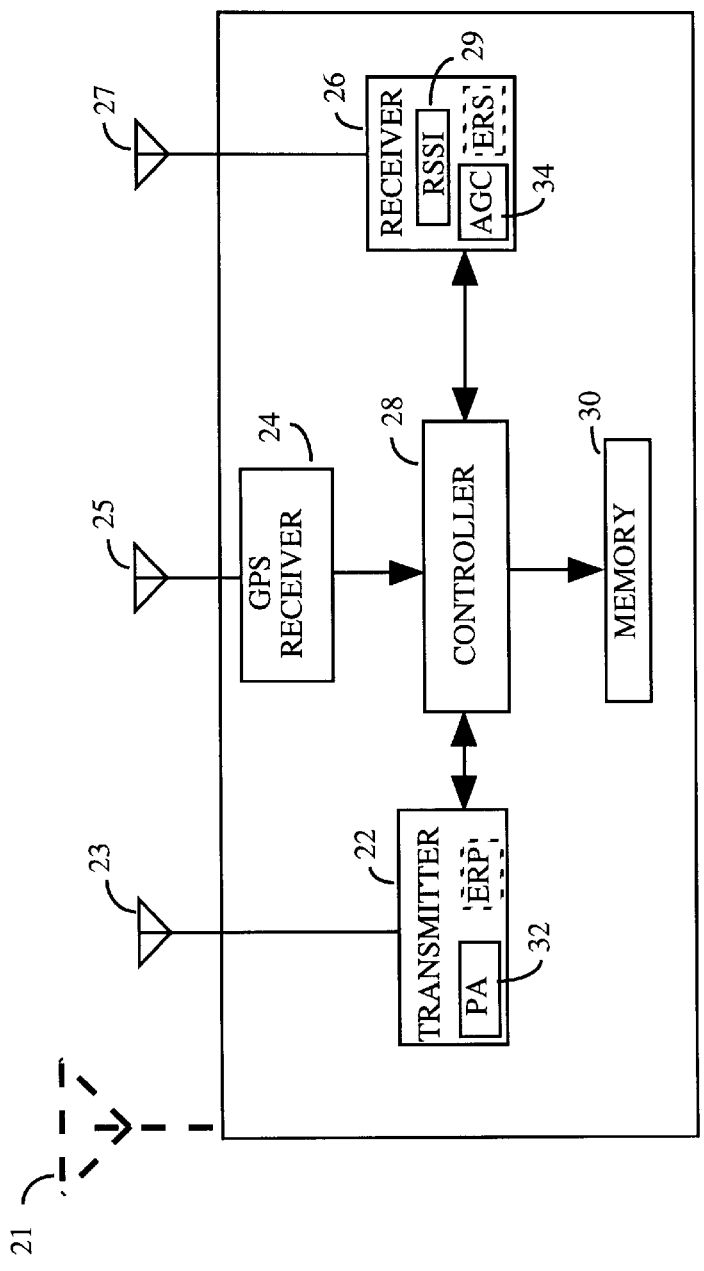
FIG. 2 is a block diagram of a transceiver in accordance with the present invention.

Referring to FIG. 2, a selective call transceiver 20 preferably comprises a receiver module 26, a controller 28 coupled to the receiver module 26 and a transmitter module 22, wherein the controller controls the operation of the selective call transceiver 20. The selective call receiver further comprises a GPS receiver 24 coupled to the controller 28 for receiving GPS information. The controller 28 uses the GPS information to assist in the control of one or more functions selected from the group of transmitter power control, site selection switching, sub-zone selection switching, forward error correction, retry transmission decisions, Doppler frequency shifting, synchronization, or frequency scanning & selection. The GPS receiver 24 provides geographic information and timing information for all these functions, but generally for transmitter power control, site selection switching and sub-zone selection switching, the GPS receiver provides geographic information which is compared with site coordinates of transmitters or base receiver in the messaging system in order to adjust the power from the transmitter module 22 via an adjustment to the power amplifier 32. The site coordinates are preferably stored within a memory location 30 within the selective call transceiver 20. The site coordinates can be preferably stored in a database or look-up table and may alternatively be stored at a memory location 91 (FIG. 4) at an outbound transmitter station 90. Additionally or alternatively, the memory locations (30 or 90) could store coordinates of desirable as well as undesirable sources that may potentially cause interference. Thus, if the selective call transceiver is near a desirable transmitter, yet also within the proximity of a known source of adjacent channel interference, the system could adjust (or probably not adjust in this case) the power coming from the desirable transmitter to overcome the adjacent channel interference.

Alternatively or in addition to the adjustment at the transmitter module 22, the gain at a Automatic Gain Controller (AGC) 34 within the receiver module 26 can be adjusted to optimize a communications system using the selective call transceiver 20. If the power level received at the receiver 26 is high, the AGC 34 can reduce the gain and provide additional battery savings at the portable subscriber unit or selective call transceiver 20. If the power from a base transmitter is reduced to limit intermodulation or if the outbound signal is weak to begin with, then the gain at the AGC 34 can be increased. Thus, in this instance, overall system performance is improved at the expense of a little battery life at a subscriber unit. Optionally, the receiver module 26 further includes an RSSI unit 29 to measure or estimate the received signal strength of incoming signals.

System performance could be further enhanced in systems using signal quality measurements where base transmitter power could be reduced based on those measurements. Transmitting only at the power required to decode at a receiver (or receiver portion of a transceiver) improves Carrier to Interference levels, reuse capabilities, measurement accuracy as well as capacity. When transmitting with too much power, there may be a tendency to overload the AGC when doing a signal quality measurement. Using GPS, the base transmitter could lower its power when the unit is close to the base transmitter site to reduce the AGC saturation and the improve signal quality measurement.

Note that the selective call transceiver 20 shows separate antennas 23, 25, and 27 for the transmitter 22, GPS receiver 24, and receiver 26 respectively. It is well know in the art to use one antenna for both the receiver 26 and transmitter 22. Alternatively, the selective call transceiver 20 uses only one antenna 21 instead of the three separate antennas. It should be appreciated that multiple antennas may be housed in the same case.

Figure 3:
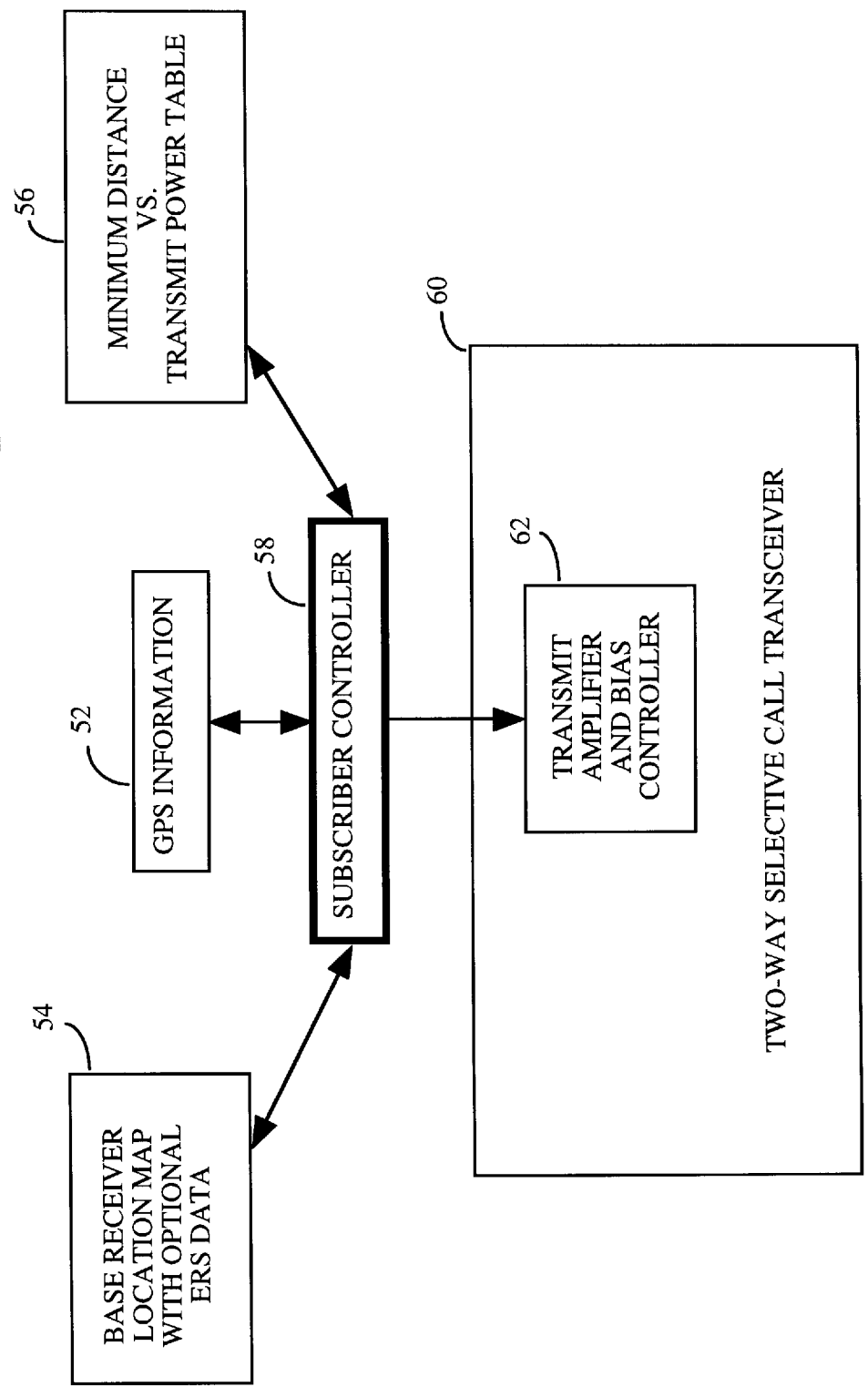
FIG. 3 is a system block diagram of a two-way paging system in accordance with the present invention.

Referring to FIG. 3, if a GPS receiver within a communication system 50 providing GPS information 52 is placed inside a mobile subscriber such as the two-way selective call transceiver 60 or at least provides the GPS information 52 to the transceiver 60, then the known GPS position of the subscriber could be used to determine the range to the nearest local base receiver. The locations of the nearest base receivers would be stored in a code plug table preferably in the form of a base receiver location map 54. The minimum distance to a receiving base station would easily be calculated from the GPS information. A subscriber controller 58 coupled to the selective call transceiver 60 would preferably reference a Minimum Distance vs. Transmit Power Table 56 to determine the required power amplifier settings and the transmit output power level would then be adjusted using the transmit amplifier and bias controller 62. In this way, the subscriber controller 58 reduces the amplitude of the subscriber output power, saving battery life.

Figure 4:
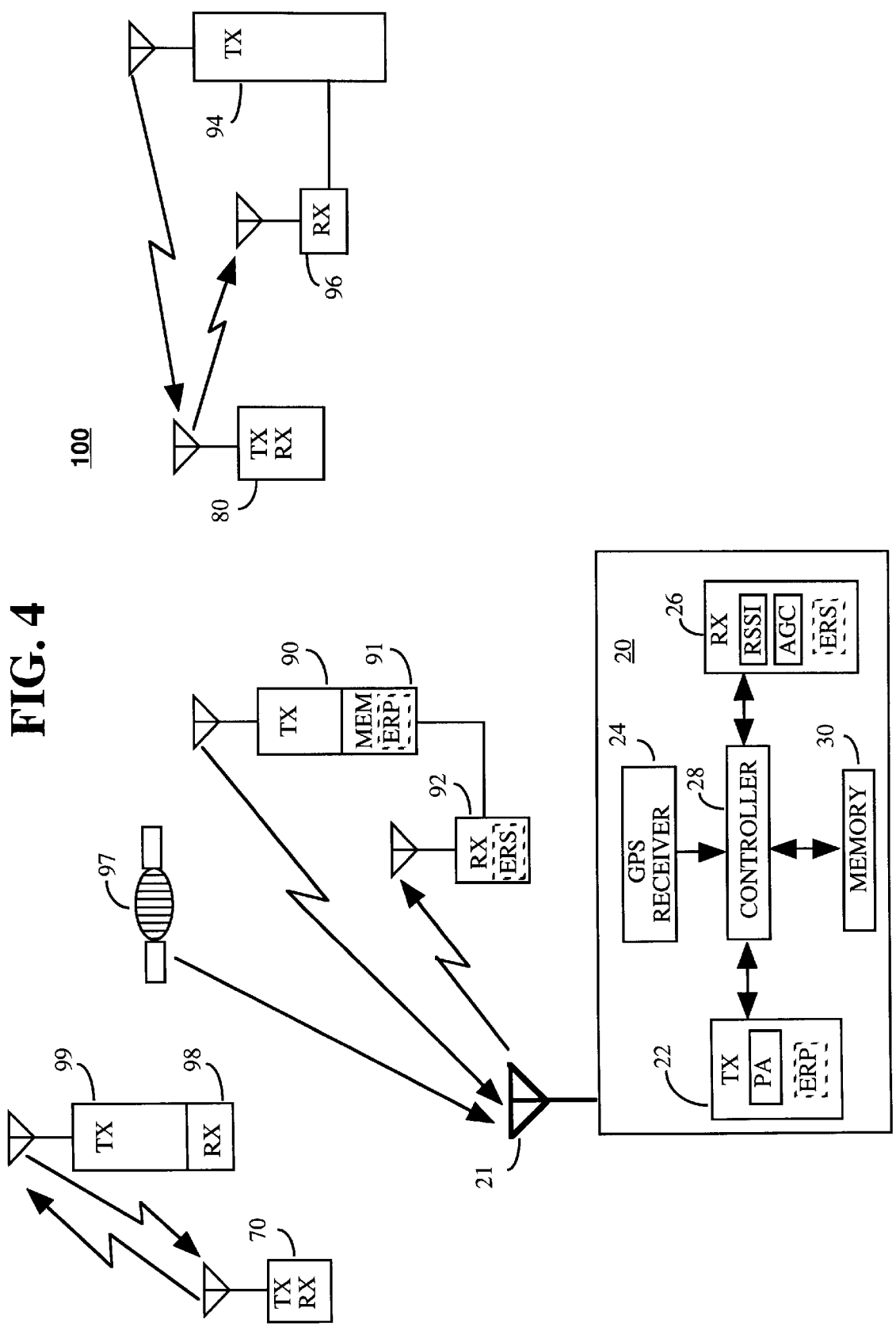
FIG. 4 is another system block diagram of a two-way paging system in accordance with the present invention.

Referring now to FIG. 4, a messaging system 100 is shown having a plurality of transmitters 90, 94 and 99, a plurality of selective call transceivers 20, 80 and 70 which communicate with the plurality of transmitters respectively, and a plurality of base receivers 92, 96, and 98 which can either be separately located from a transmitter or co-located with a transmitter as shown with base transmitter 99 and base receiver 98 combination. Preferably, the selective call transceivers 20, 70 and 80 are either the same or similar to the selective call transceiver 20 described with respect to FIG. 2.

In one embodiment, a GPS satellite 97 provides the GPS receiver 24 at the selective transceiver 20 provides geographic information which is compared with site coordinates of transmitters in the messaging system 100 in order to adjust the power from at least one (90) of the plurality of transmitters transmitting to the selective call transceiver. In this instance, GPS information could be sent inbound from the selective call transceiver 20 to the messaging system to allow the system to make decisions base on the geographic information. Again the site coordinates can either be stored within a memory location 30 within the selective call transceiver 20 or at a memory location 91 at an outbound transmitter station 90. In a further refinement of the present invention, the selective call transceiver 20 could use RSSI measurements along with the geographic information to make adjustments to the power either at the transmitter module 22 or from the transmitter 90. In yet another embodiment, the geographic information can be used to adjust both the outbound power transmission from at least one (90) of the plurality of transmitters transmitting to the selective call transceiver 20 and the inbound power transmission from the selective call transceiver 20.

Use of the GPS information at the subscriber not only aides in power control, but for site selection switching, sub-zone selection switching, forward error correction, retry transmission decisions, Doppler frequency shifting, synchronization, frequency scanning and frequency selection. In the case of where synchronization with a messaging system is lost, it can take several minutes to reacquire synchronization in a typical system. But if a subscriber unit is coupled with a GPS receiver, synchronization can be maintained during times of lost system coverage since the GPS information signal includes an accurate time signal. Knowledge of direction and velocity of the subscriber unit is advantageous to forward error correction algorithms, frequency reuse plan selections, re-try methods and to subzone selection switching. With respect to forward error correction, different forward error correction schemes work best at different velocities. Therefore, one embodiment of the present invention could certainly include changing forward error correction schemes depending on the velocity determined. Thus, a subscriber unit coupled with a GPS receiver would provide these advantages since velocity can be accurately determined. Knowledge of the position of the subscriber unit has additional benefits for retransmissions. For instance, since a subscriber unit with a GPS receiver could identify its location, there is no need to send a "where are you" (WRU) request from the base station transmitter. Another example is the prevention of wasteful re-transmissions into an existing site when the system has knowledge of the velocity and direction of the subscriber so that a useful re-transmission is sent to an adjacent site where the subscriber is project to travel.

Two-way paging systems such as InFLEXion™ and ReFLEX™ utilize targeted messaging. Current methods utilizing color codes or RSSI have low probability of finding the right transmitter. Coupled with GPS and a database of site coordinates stored in either the subscriber unit or system controller, the subscriber unit could be able to select the proper transmitter with higher accuracy. This may also be extended to the choice of subzones as a user moves throughout a coverage area as well as even knowing which city the user has arrived in for frequency scanning time reduction.

With respect to Doppler frequency shifting, a subscriber unit will either transmit or receive off-frequency by a given amount based on the velocity the subscriber unit is traveling relative to the base transmitter or base receiver. If the subscriber unit is transmitting and traveling toward a base receiver at 70 miles per hour, then an inbound transmission at 900 MHz will suffer a Doppler shift of approximately 94 Hz which can be accounted for by either adjusting a local oscillator to reduce the transmission frequency at the subscriber or increase the receive frequency at the base receiver. The Doppler shift is easily calculated as follows: $Cos(\theta) \times 1.49 \times V \text{ [mph]} \times F \text{ [Ghz]} = 1.49 \times 70 \times .9 = 93.87$ Hz, where $\theta$ is the angle created by a line connecting the portable subscriber unit to the base site and a line indicating the direction of travel (we assume $Cos(\theta)=1$ in our example). This then provides the plus (+) or minus (−) indication for increasing or decreasing frequency. Since the GPS knows the direction of travel and the portable subscriber location and the base station location is known, all the information is known to determine the angle $\theta$. Likewise, if the subscriber unit is traveling away from a base receiver, then the Doppler shift can be accounted for by either adjusting a local oscillator to increase the transmission frequency at the subscriber or reduce the receive frequency at the base receiver. Correspondingly, if a base transmitter is transmitting to a subscriber unit that is approaching at 70 miles per hour, then the outbound transmission at 900 MHz will again suffer a Doppler shift of approximately 94 Hz which can be accounted for by either adjusting a local oscillator to reduce the transmission frequency at the base transmitter or increase the receive frequency at the subscriber unit's receiver. Likewise, if the subscriber unit is traveling away from a base transmitter, then the Doppler shift can be accounted for by either adjusting a local oscillator to increase the transmission frequency at the base transmitter or reduce the receive frequency at the subscriber unit's receiver. The frequency may be altered by changing the control voltage at a transmitter or receiver VCO (not shown) within the subscriber or base station.

Figure 5:
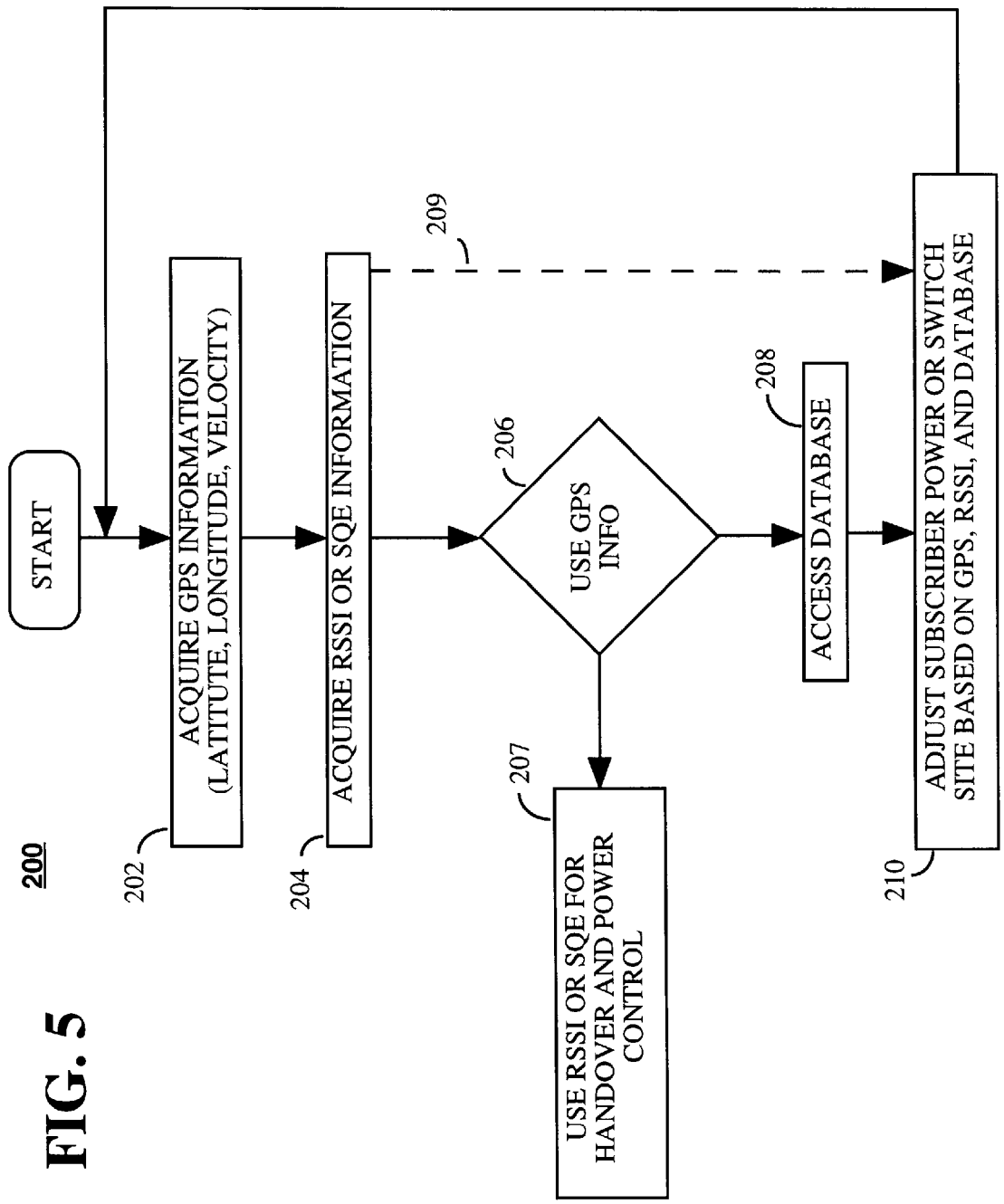
FIG. 5 is a flow chart of a method for geographic based control in a communication system in accordance with the present invention.

Referring to FIG. 5, method 200 of controlling the operation of a two-way selective call subscriber device having a GPS receiver within a messaging system having a plurality of transmitters having known coordinates is shown. The method 200 comprises at step 202 of acquiring GPS information at a selective call receiver from the GPS receiver comprising information selected from the group of latitude, longitude, and velocity. At step 204, the two-way selective call subscriber device acquires a received signal strength measurement. At decision block 206, the method 200 determines whether to use the GPS information. If the GPS information is to be used, then at step 208 a look-up table of the known transmitter coordinates is accessed and compared with the known transmitter coordinates with the GPS information. Finally, at step 210, the operation of the messaging system is controlled based on the GPS information, the received signal strength measurement and the known transmitter coordinates. If at decision block 206 it is determined not to use the GPS information, then use of RSSI or SQE is used for handover and power control at step 207. Alternatively, the decision block 206 can be bypassed and path 209 can be followed to step 210 to adjust the subscriber power or switch sites directly after acquiring the GPS information and RSSI or SQE information in steps 202 and 204 respectively.

The step of controlling the operation of the messaging system at step 210 could comprise adjusting the power of a transmitter within a two-way selective call subscriber device and/or adjusting the power of one or more of the plurality of transmitters within the messaging system to the two-way selective call subscriber device. The step of controlling the operation of the messaging system could also comprise adjusting the power of a automatic gain controller within the two-way selective call subscriber device. The step of controlling the operation of the messaging system could also comprise of switching to a new site or a subzone.

The present invention is not only applicable to a two-way paging system, but could equally apply to other communication systems such as Motorola's iDEN, SmartZone, Coverage Plus systems as well as other dispatch, cellular and data systems. With the present invention, using GPS location information and the site coordinates at a subscriber units allows for automated switching, handover, or targeted message delivery without a manual switching by a user. In wide area systems, such as iDEN or Cellular, geographic switching could eliminate some overhead or pilots or could be used in addition to this information for more accurate site switching or handover. For systems such as AMSS or SmartZone, geographic switching could also be used in place of, or in addition to RSSI switching. These are but a small sampling of the added benefits that existing communication systems could obtain by incorporating the present invention.

As a final example of the wide applicability of GPS information at a portable subscriber unit, the present invention could also be used in aiding the adjustment of the output power based on determining the difference in link margin between outbound and inbound traffic to the same site as described in U.S. Pat. No. 5,257,408, incorporated herein by reference. If the base transmitters can embed in a signal its (a) Effective Radiated Power (ERP) and (b) the base receiver's effective receiver sensitivity (ERS), and a portable subscriber unit knows (c) its ERP and (d) its ERS, then the outbound link ((a)–(d)) and the inbound link ((c)–(b)) can be calculated. This difference, out—in represents the difference in link budgets that can be used as a method to reduce the ERP of the subscriber unit to save battery life without reducing reliability. In one embodiment using this method, the site coordinates of base receivers as well as the ERS associated with the site coordinates could be stored within the portable subscriber unit (see FIGS. 2 and 3). Thus, the subscriber unit having knowledge of its location from GPS information, can then choose and/or calculate the best base receiver to transmit to that requires the least transmission power from the portable subscriber based on distance and the ERS of the associated base receiver. Of course, the base transmitters could preferably and just as easily transmit the base receiver coordinates and the base receiver's associated ERS to the subscriber units (see FIG. 4) if memory is limited or constrained at the subscriber unit or if an entire base receiver coordinate list or database is impractical, particularly for a roaming subscriber unit.

It should be understood that the disclosed embodiments are merely examples and the invention is not restricted thereto. It will be understood by those skilled in the art that variations and modifications can be made within the scope and spirit of the present invention as defined by the appended claims.

What is claimed is:

1. A selective call transceiver in a communication system having a plurality of transmitters, comprising:
   a receiver module;
   a transmitter module coupled to the receiver module;
   a controller coupled to the receiver module and the transmitter module for controlling the operation of the selective call transceiver; and
   a GPS receiver for receiving GPS information and coupled to the controller, wherein the controller uses the GPS information to assist in the control of functions selected from the group consisting of transmitter power control, site selection switching, sub-zone selection switching, forward error correction, and retry transmission decisions, wherein the function of transmitter power control uses the transmitter module to transmit to base receivers within the messaging system information derived from geographic information from the GPS receiver and site coordinates of transmitters in the messaging system in order to adjust the power of transmitters selected from the group consisting of the transmitter module and the at least one of the plurality of transmitters transmitting to the selective call transceiver.

2. The selective call transceiver of claim 1, wherein the site coordinates are stored within a memory location within the selective call transceiver.

3. The selective call transceiver of claim 1, wherein the selective call transceiver uses Received Signal Strength Indications along with the geographic information to adjust the power from the transmitter module.

4. The transceiver of claim 1, wherein the GPS receiver provides geographic information which is compared with site coordinates of transmitters in the communication system in order to adjust an outbound power transmission from at least one of the plurality of transmitters transmitting to the transceiver and to adjust an inbound power transmission from the transceiver.

5. The selective call transceiver of claim 4, wherein the site coordinates are stored with a memory location within a system controller remote from the selective call transceiver but within the messaging system.

6. The selective call transceiver of claim 1, wherein the GPS receiver provides timing information to the receiver module to maintain synchronization with the messaging system.

7. The selective call transceiver of claim 1, wherein the GPS receiver is used to determine direction and velocity of the selective call transceiver to aide in functions selected from the group of forward error correction, retransmission decisions, Doppler frequency shifting and subzone selection switching.

8. A selective call transceiver, comprising:
a receiver module having an automatic gain controller;
a transmitter module coupled to the receiver module and further having a power amplifier, wherein the transmitter transmits data to a messaging system;
a controller coupled to the receiver module and the transmitter module for controlling the operation of the selective call transceiver; and
a GPS receiver coupled to the receiver module and the transmitter module, wherein a radio received signal strength indication and location information from the GPS receiver is used to control the gain at the automatic gain controller and to control transmit power at the power amplifier, wherein the GPS receiver also provides geographic information which is compared with site coordinates of transmitters in the messaging system allowing at least one of the plurality of transmitters transmitting to the selective call transceiver to adjust its power to the selective call transceiver based on data derived from the geographic information and the site coordinates.

9. The selective call transceiver of claim 8, wherein the GPS receiver provides geographic information which is compared with site coordinates of transmitters in the messaging system in order to adjust an outbound power transmission from at least one of the plurality of transmitters transmitting to the selective call transceiver and to adjust an inbound power transmission from the selective call transceiver.

10. The selective call transceiver of claim 9, wherein the site coordinates are stored within a memory location within the selective call transceiver.

11. The selective call transceiver of claim 9, wherein the site coordinates are stored within a memory location within a system controller remote from the selective call transceiver but within the messaging system.

12. A selective call transceiver in a messaging system having a plurality of transmitters, comprising:
a receiver module;
a transmitter module coupled to the receiver module;
a controller coupled to the receiver module and the transmitter module for controlling the operation of the selective call transceiver;
a GPS receiver for receiving GPS information and coupled to the controller, wherein the controller uses the GPS information to assist in the control of functions selected from the group consisting of transmitter power control, site selection switching, sub-zone selection switching, forward error correction, retry transmission decisions, Doppler frequency shifting, synchronization, and frequency scanning and selection;
a received signal strength indicator coupled to the receiver module and the controller for providing a measurement of received signal strength for a given one of the plurality of transmitters; and
a memory for storing site coordinates corresponding to the plurality of transmitters, wherein the geographic information is compared with the site coordinates along with the received signal strength measurement to adjust the power from at least one of the plurality of transmitters for optimum efficiency.

13. The selective call transceiver of claim 12, wherein the GPS receiver is used to determine direction and velocity of the selective call transceiver to aide in adjusting for a Doppler frequency shift in a transmitting frequency from the transmitter module as the selective call transceiver travels at a measured velocity towards one of the plurality of transmitters that is transmitting to the selective call transceiver.

14. A method of controlling the operation of a two-way selective call subscriber device having a GPS receiver within a messaging system having a plurality of transmitters having known coordinates, comprising the steps of:
acquiring GPS information from the GPS receiver comprising information selected from the group of latitude, longitude, and velocity;
acquiring a received signal strength measurement at the two-way selective call subscriber device;
accessing a look-up table of the known transmitter coordinates and comparing the known transmitter coordinates with the GPS information; and
adjusting the power of at least one of the plurality of transmitters within the messaging system communicating with the two-way selective call subscriber device based on the GPS information, the received signal strength measurement and the known transmitter coordinates.

15. The method of claim 14, wherein the step of controlling the operation of the messaging system comprises adjusting the power of a transmitter within the two-way selective call subscriber device.

16. The method of claim 14, wherein the step of controlling the operation of the messaging system comprising adjusting the power of one or more of the plurality of transmitters within the messaging system communicating to the two-way selective call subscriber device as well as adjusting the power of a transmitter within the two-way selective call subscriber device.

17. The method of claim 14, wherein the step of controlling the operation of the messaging system comprises adjusting the power of a automatic gain controller within the two-way selective call subscriber device.

18. The method of claim 14, wherein the step of controlling the operation of the messaging system comprises switching to a new site or subzone.

19. A method of controlling the operation of a two-way selective call subscriber device having a GPS receiver within a messaging system having a plurality of base receivers with known coordinates, comprising the steps of:

acquiring GPS information from the GPS receiver comprising information selected from the group of latitude, longitude, and velocity;

acquiring a base receiver sensitivity measurement of at least one of the plurality of base receivers at the two-way selective call subscriber device; and controlling the operation of the messaging system based on the GPS information and the base receiver sensitivity measurement, wherein the step of controlling comprises selecting the at least one of the plurality of base receivers having the closest distance between the base receiver and the two-way selective call subscriber device using the GPS information and adjusting a power level transmitted from the two-way selective call subscriber device to the selected base receiver based on knowledge of the base receiver's sensitivity.

20. The method of claim 19, wherein the base receiver's sensitivity is stored within a memory within the two-way subscriber device.

21. The method of claim 19, wherein the base receiver's sensitivity is transmitted by a base transmitter to the two-way subscriber device.

* * * * *